United States Patent
Jordan et al.

(10) Patent No.: US 9,829,416 B2
(45) Date of Patent: Nov. 28, 2017

(54) CLOSURE WITH SEPTUM STRIP

(71) Applicant: Roche Molecular Systems, Inc., Pleasanton, CA (US)

(72) Inventors: Aaron Jordan, Zug (CH); Willem Mulder, Baar (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 1132 days.

(21) Appl. No.: 13/774,769

(22) Filed: Feb. 22, 2013

(65) Prior Publication Data

US 2013/0224868 A1    Aug. 29, 2013

(30) Foreign Application Priority Data

Feb. 24, 2012   (EP) .................................. 12156885

(51) Int. Cl.
*G01N 1/28* (2006.01)
*B01L 3/00* (2006.01)
*B65D 51/00* (2006.01)

(52) U.S. Cl.
CPC ............ *G01N 1/28* (2013.01); *B01L 3/50853* (2013.01); *B01L 3/50855* (2013.01); *B01L 3/523* (2013.01); *B01L 2200/0689* (2013.01); *B01L 2200/141* (2013.01); *B01L 2300/04* (2013.01); *B01L 2300/042* (2013.01); *B01L 2300/044* (2013.01); *B01L 2300/049* (2013.01); *Y10T 436/119163* (2015.01)

(58) Field of Classification Search
CPC ........ G01N 1/28; G01N 1/00; B01L 3/50853; B01L 3/508; Y10T 436/11; Y10T 436/119163; B65D 51/002; B65D 51/00
USPC .................. 436/54, 43; 73/864.63, 864, 63; 220/23.2; 215/247, 274, 273, 200, 355
See application file for complete search history.

(56) References Cited

U.S. PATENT DOCUMENTS

| | | | | |
|---|---|---|---|---|
| 3,713,771 A | * | 1/1973 | Taylor | A61B 10/00 141/378 |
| 5,005,721 A | * | 4/1991 | Jordan | B01L 3/50853 220/23.4 |
| 6,024,235 A | * | 2/2000 | Schwab | B65D 51/002 215/247 |
| 6,752,965 B2 | | 6/2004 | Levy | |

(Continued)

FOREIGN PATENT DOCUMENTS

| EP | 0504697 A1 | 9/1992 |
|---|---|---|
| EP | 0504697 B1 | 9/1992 |

(Continued)

*Primary Examiner* — Christine T Mui
(74) *Attorney, Agent, or Firm* — Pamela C. Ancona; M. Reza Savari

(57) ABSTRACT

A closure is described for a container containing a reagent. The closure includes a cover. The cover includes at least two through bore holes. The closure further includes a strip which includes a base and at least two septa. The base is of a stiff material and the septa is of a flexible material. The septa are attached to one surface of the base. Each septum includes a pre-slit bottom and a barrel forming the sides of the septum. The outer diameter of each septum barrel is larger than the inner diameter of the through bore hole such that a pressure is exerted on the septum when the septum is press fitted into the through bore hole.

14 Claims, 5 Drawing Sheets

(56) References Cited

U.S. PATENT DOCUMENTS

| | | | |
|---|---|---|---|
| 7,537,935 B2* | 5/2009 | Bienhaus | B01L 3/5025 |
| | | | 210/198.2 |
| 7,790,115 B2 | 9/2010 | Sogaro | |
| 8,372,353 B2 | 2/2013 | Lee et al. | |
| 2009/0308184 A1* | 12/2009 | Blekher | A61B 5/1411 |
| | | | 73/864.63 |

FOREIGN PATENT DOCUMENTS

| | | |
|---|---|---|
| EP | 0836884 A2 | 4/1998 |
| EP | 0836884 A3 | 1/1999 |
| EP | 1122181 A2 | 8/2001 |
| EP | 1122181 A3 | 8/2001 |
| WO | 9301739 A1 | 2/1993 |
| WO | 9511083 A2 | 4/1995 |
| WO | 9511083 A3 | 4/1995 |
| WO | 0121310 A2 | 3/2001 |
| WO | 0121310 A3 | 3/2001 |

* cited by examiner

CLOSURE WITH SEPTUM STRIP

CROSS-REFERENCES TO RELATED APPLICATIONS

The present application claims the benefit of priority under 35 U.S.C. §119 of EP12156885.1, filed Feb. 24, 2012, the content of which is incorporated by reference herein in its entirety.

FIELD OF THE INVENTION

The present invention relates to closures for containers containing reagents. Such containers are useful for automated analytical systems and automated analyzers. In such systems, containers contain reagents that are necessary for the analytical process performed within the analyzer. The reagents are transferred from the containers to receptacles in which at least parts of the analytical processes are performed using automated pipetting systems. Thus, the present invention also relates to automated methods and systems of pipetting reagents held by such containers.

SUMMARY OF THE INVENTION

The present invention provides a closure for a container containing a reagent. Said closure comprises a cover. The cover comprises at least two through bore holes. The closure further comprises a strip which comprises a base and at least two septa. The base consists of a stiff material and the septa consist of a flexible material. The septa are attached to one surface of the base. Each septum comprises a pre-slit bottom and a barrel forming the sides of the septum. The outer diameter of each septum barrel is larger than the inner diameter of the through bore hole such that a pressure is exerted on the septum when the septum is press fitted into the through bore hole.

The present invention further relates to a container comprising a vessel for holding a reagent. The vessel has a closed bottom end and an open top end, and a closure as described above.

The present invention also provides a method of pipetting a reagent in an automated analyzer, said method comprising the steps of providing to the automated analyzer a container as described above, wherein the closure of said container comprises press fitted pre-slit septa, penetrating said pre-slit septa with blunt ended pipetting devices, wherein each of the pre-slit septa comprises a slit which is longer than the diameter of each of said pipetting devices such that a pressure relief occurs upon penetration, aspirating a predetermined volume of said reagent into said pipetting device, removing said blunt-ended pipetting device, whereby a pressure exerted by the through-bore hole on the press-fitted pre-slit septum causes the pre-slit septum to close, dispensing the aspirated reagent into a vessel.

Furthermore, a system for pipetting reagents in an automated analyzer is provided comprising the container of the present invention and a pipettor for aspirating and dispensing reagents, wherein said pipettor is operatively coupled to a blunt-ended pipetting device.

BRIEF DESCRIPTION OF THE FIGURES

Other and further objects, features and advantages of the invention will appear more fully from the following description. The accompanying drawings, together with the general description given above and the detailed description given below, serve to explain the principles of the invention.

DETAILED DESCRIPTION OF THE INVENTION

Figure 1:
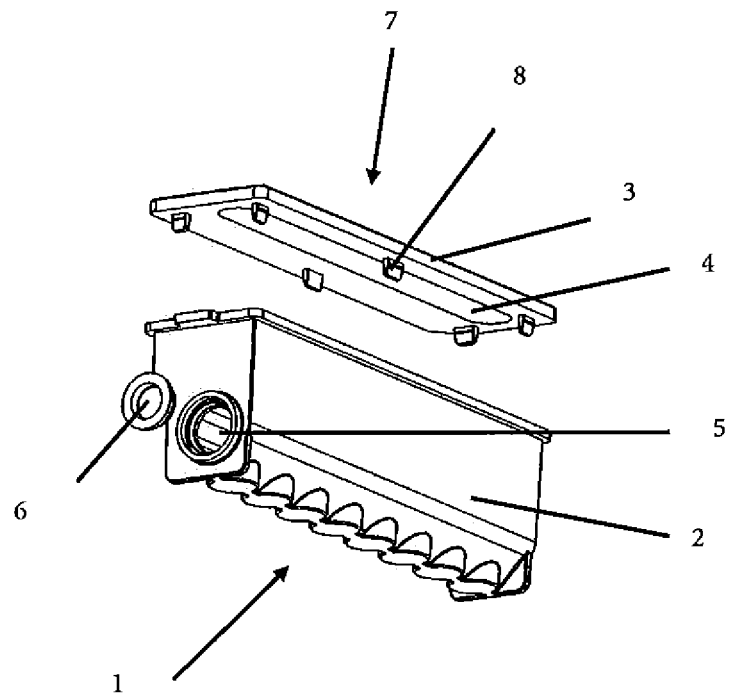
FIG. 1 shows a perspective view of the container comprising a closure and vessel.

The present invention provides a closure for a container holding a reagent. Said closure comprises a cover. The cover comprises at least two through bore holes. The closure further comprises a strip which comprises a base and at least two septa. The base consists of a stiff material and the septa consist of a flexible material. The septa are attached to one surface of the base. Each septum comprises a pre-slit bottom and a barrel forming the sides of the septum. The outer diameter of each septum barrel is larger than the inner diameter of the through bore hole such that a pressure is exerted on the septum when the septum is press fitted into the through bore hole.

The term "closure" as used herein relates to a structure which can close an open end of a container. Such a closure prevents contaminants from the outside from contaminating the reagent held in the container, in particular in cases where such contaminants can easily be spread by aerosols or droplets. Closures may be removed before the reagents held in the container are accessed. In order to optimize the prevention of contamination and at the same time provide accessibility of the reagent held in the container during pipetting, the closure remains attached to the container and comprises re-sealable openings which open when penetrated by a pipette device and close again automatically when the pipette device is removed.

The closure comprises an upper surface which, when mounted, faces the outside of the container, e.g., the pipettor; and a lower surface which faces the inside of the container when the cover is attached to the container. In addition, the closure comprises elements that allow it to be attached to the container. Such elements may be snap fit elements or other elements know to the skilled person.

The term "cover" as used herein relates to one part of the closure. The cover consists of a stiff material, e.g., of polypropylene. The cover provides a stable upper part of the closure which can support a more flexible penetrable material used to access the contents of the container.

The term "container" as used herein relates to a hollow body with a vessel capable of holding a reagent and a closure. The term "vessel" thus relates to a part of the container which has an open top and a closed bottom and which holds the reagent. The container may comprise other additional features. For example, the container may also comprise an opening for filling reagents into the container before use in the analytical instrument. Such an opening may be closed using a closure, e.g., a cap which can be attached to the opening. The attachment may be reversible. However, the type of attachment has to provide a liquid tight closing of the opening. This closure is not removed while the container is located in the analyzer.

The term "reagent" as used herein relates to any type of liquid which has to be transferred during an analytical process. Thus, the term includes liquid samples. It also includes liquid reagents and suspensions comprising solid particles. Reagents include diluents, wash buffers, liquid compositions required for isolating, purifying, enriching, extracting analytes and reagents necessary for reacting analytes, such as reagents for nucleic add amplification and reagents necessary to obtain a detectable signal.

The term "through bore hole" as used herein relates to a cylindrical extension located at a circular opening in the cover of the closure. The through bore hole may, thus, also be called a cylindrical extension. The through bore hole comprises a cylindrical wall formed of a stiff material. One such material is polypropylene. In one embodiment, the through bore hole is formed of the same material as the cover. The cylindrical extensions of two or more through bore holes located on one cover extend from the surface of the cover which faces the inside of the container.

The term "strip" as used herein relates to a part of the closure which comprises a base and at least two septa attached to the base.

The term "base" as used herein relates to a support making up part of the strip. The base comprises an upper surface which, as part of the closure, faces the outside of the container, and a lower surface which, when the closure is assembled, faces the cover of the closure. The base supports at least two septa. The at least two septa are attached to the lower surface of the base. The lower surface of the base is the surface which, when the base is fitted into the cover, faces the cover surface. The distance between two septa on the base corresponds to the distance between two through bore holes on the cover. The base is made of a stiff material. The stiff material of the base provides stability to the strip of septa. This allows to more quickly and precisely assemble and press fit the strip comprising the base and septa into the through bore holes of the cover.

The term "septum" as used herein relates to a penetrable seal for containers. The term "septa" is used as the plural of the term "septum". A septum comprises one or more flexible materials which are penetrable for needles and/or pipetting devices. The septum comprises a barrel forming its sides. On the outer side of the septum which contacts the through bore hole, the septum has the same shape as the through bore hole. For example, if the through bore hole has a cylindrical shape, the outer side of the barrel is also cylindrical. The inner side of the barrel may be cylindrical, but may also have a different shape, e.g., a conical shape, e.g., a frustum. In one embodiment, the septum has a pre-slit bottom. The slit facilitates penetration of a needle or pipette device. Blunt needles and blunt pipette devices can more easily penetrate the septum. The term "pre-slit bottom" as used herein relates to the slit already present in the septum before penetration with a needle or pipette device. The bottom of the septum is the part which faces the inside of the container. In one embodiment, the slit is longer than the diameter of needle or pipetting devices such that a pressure relief occurs upon penetration. "Pressure relief" means that if the pressure inside the closed container is different from the environmental pressure, the pressure will become equalized by the pressure relief. This pressure relief ensures precise pipetting by equalizing pressure in and outside the container.

When the strip comprising the base and the septa attached to the base is assembled with the cover of the closure, the septa are fitted into the through bore holes. The outer diameter of a septum barrel is larger than the inner diameter of the through bore hole that the septum is fitted into. The term "outer diameter of the septum barrel" as used herein relates to the diameter measured from the surface of the septum barrel that contacts the through bore hole. The term "inner diameter of the through bore hole" as used herein relates to the diameter measured from the surface of the through bore hole that contacts the septum. As the septum made of a flexible material is fitted into the through bore hole made of a stiff material, a pressure is exerted onto the septum due to the larger outer diameter of the septum, compared to the inner diameter of the through bore hole. By this pressure, the septum is press fitted into the through bore hole. The press fit causes the septum to close firmly when the pipetting device is removed from the septum again. This prevents contaminations from outside entering the container, and loss of liquid in the container, e.g., by evaporation or spillage or aerosol formation.

In one embodiment, the outer diameter of said septum is up to 50% larger than the inner diameter of the through bore hole. In another embodiment, the outer diameter of said septum is up to 20% larger than the inner diameter of the through bore hole.

The term "stiff material" as used herein relates to materials that confer stiffness to the structure they form. Stiff materials include glass or stiff polymers. It may comprise one or more components.

In one embodiment, the stiff material of the base of the strip comprises polypropylene or a thermoplastic polymer. The cover of the closure and the vessel of the container may be made of the same material, or of a different material.

The term "flexible material" as used herein relates to a material which is flexible and which is penetrable by needles or other pipetting devices. In one embodiment, the material is penetrable by blunt ended needles or pipetting devices.

In one embodiment the septa comprise TPE or rubber. The septa may comprise one or more components.

When the closure is assembled, the strip comprising the base and septa is assembled with the cover of the closure such that the septa are press fitted into the through bore holes and the side of the base facing the cover contacts the cover.

The base of the strip is then bonded to the closure. This results in a closure with septa press fitted into the through bore holes and the base of the strip bonded to the cover of the closure. This ensures that the strip can not be accidentally removed, e.g., when retracting the pipetting devices after aspirating liquid from within the container.

The stiff material of the base allows to more precisely bond the base of the strip to the cover. This is due to the lack of deformation of the stiff material of the base of the strip during bonding of the base and the cover.

In one embodiment, the closure comprises an upper and a lower surface, wherein the upper surface is covered by a sealing foil. In one embodiment the sealing foil is aluminum. The sealing foil may also be a foil comprising more than one material.

The present invention also relates to a container comprising a vessel for holding a reagent wherein said vessel has a closed bottom end and an open top end, and a closure as described herein. In one embodiment more than one container can be placed within a cassette. In a specific embodiment the cassette comprises a base having an average length and an average width, wherein said average length and average width are substantially corresponding to ANSI SBS format. The term "substantially" as used herein means that small deviations from the ANSI SBS format are possible, while the overall format is represented by the average length and average width of the base. The terms "average length" and "average width" are understood to mean that while, in specific positions, the length and width of the base may deviate from the ANSI SBS format, a substantial part of the positions will conform to the ANSI SBS format. The cassette further comprises recesses or openings for engagement with a handler for transporting the cassette inside an automated analyzer. Furthermore, the cassette may comprise hardware identifiers that allow the analyzer to specifically recognize the cassette based on the surface geometry of the cassette. While the assembly of the containers holding liquids makes the transport and use of the containers more easily automatable within an automated analyzer, it also provides more flexibility regarding the loading of containers with different liquids for different types of tests. This flexibility also takes better account of the different frequencies with which different tests need to be run.

The present invention also relates to a method of pipetting a reagent in an automated analyzer. The term "pipetting" relates to the transfer of liquids using a pipettor. Pipettors are devices which aspirate and/or dispense liquids and are well known to the person skilled in the art. The method comprises the following steps:

A container as described herein is provided to the automated analyzer. This means that the container is loaded either manually or automatically into the automated analyzer.

As described herein, the closure of the container comprises press-fitted pre-slit septa. The pre-slit septa, are penetrated with blunt-ended pipetting devices. The pre-slit septa comprise a slit which is longer than the diameter of each of said pipetting devices such that a pressure relief occurs upon penetration.

The term "blunt-pipetting devices" as used herein relates to pipetting devices such as needles or disposable pipette tips which have a blunt end. The blunt end is the end of the pipetting device which first penetrates the pre-slit septum. A blunt end is an end which is not sharp.

As a next step, a predetermined volume of the reagent is aspirated into the pipetting devices. Once the predetermined volume is aspirated, the blunt-ended pipetting device is removed from the septum, whereby a pressure exerted by the through bore hole on the press-fitted pre-slit septum causes the pre-slit septum to close. Then, the aspirated reagent is dispensed into a vessel.

The steps of penetrating the septa with blunt-ended pipetting devices, aspirating reagent, removing the blunt-ended pipetting devices and dispensing can be repeated at least once.

A system for pipetting reagents in an automated analyzer is also provided, comprising a container as herein before described. In one embodiment, the system comprises a cassette comprising at least two containers as described herein. The system further comprises a pipettor for aspirating and dispensing reagents, wherein said pipettor is operatively coupled to a blunt-ended pipetting device. The term "operatively coupled" means that the pipettor controls aspiration of liquid into the pipette device, and dispensing the liquid from the pipetting device.

In one specific embodiment, the system additionally comprises a transport mechanism for transporting the container to the pipettor and away from the pipettor.

In one embodiment, the system additionally comprises a storage for storing the container, wherein the container is returned to the storage after pipetting, and is transported back to the pipettor for pipetting.

Example

Figure 2:
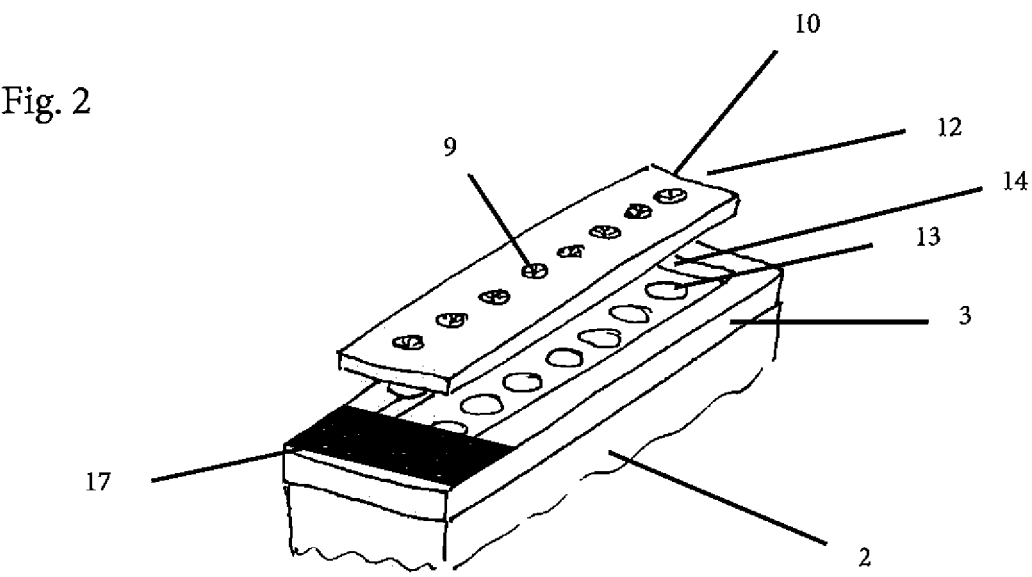
FIG. 2 shows a top view of the septa strip and the cover mounted on the upper part of the vessel, with a part of a covering the cover.
Figure 3:
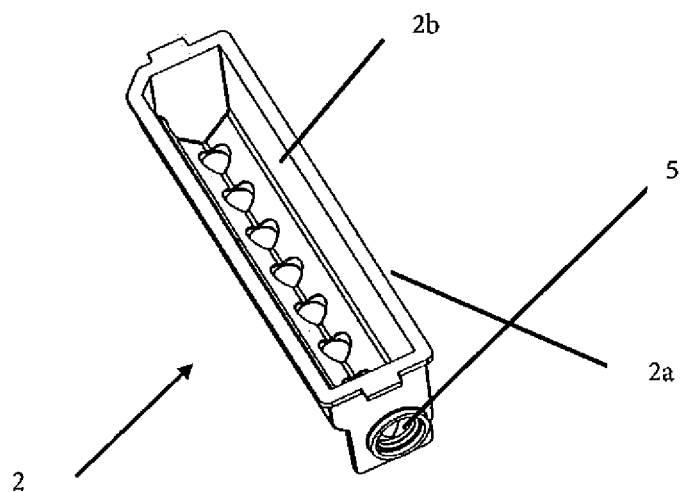
FIG. 3 shows a top view of the vessel.

Container 1 comprises vessel 2. Vessel 2 has a filling hole 5 which can be closed in a liquid tight manner with plug closure 6. Furthermore, container 1 comprises a closure 7. Closure 7 has cover 3 and positioning elements 8 to assemble and fix the closure 7 on the vessel 2. The position where the septa are located is indicated with 4 (FIG. 1). A strip 12 with eight septa 9 is shown in FIG. 2. The strip has base 10 on which the septa 9 are attached. Strip 10 is made of polypropylene. Septa 9 can be attached to strip 10 by two component molding. The cover 3 shown in FIG. 2 has eight through bore holes 13. The septa 9 can be pressure fitted into through bore holes 13 when assembling the closure 1. The pocket 14 of cover 3 has dimensions matching the outside of the base 10 such that the base 10 is seated in the pocket 14 when the strip 12 and cover 3 are assembled. The foil 17 is shown exemplary. Foil 17 is intended to cover the assembled complete closure 1. FIG. 3 shows the interior of the vessel 2 with inner side walls 2b and outer walls 2a and the filling hole 5.

Figure 4:
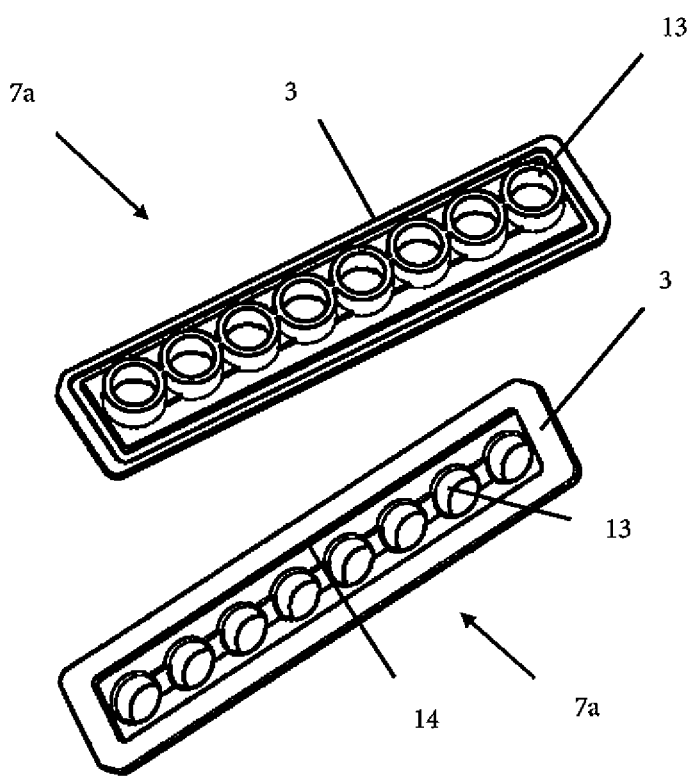
FIG. 4 shows a) a top and bottom view of the cover without the septa strip; b) a top and a bottom view of the septa strip and c) a top and a bottom view of the assembled closure.
Figure 4:
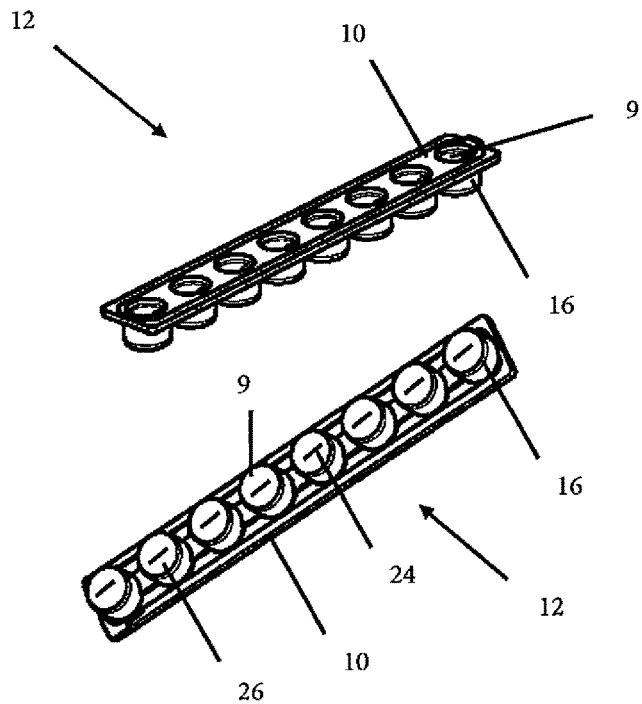
Figure 4:
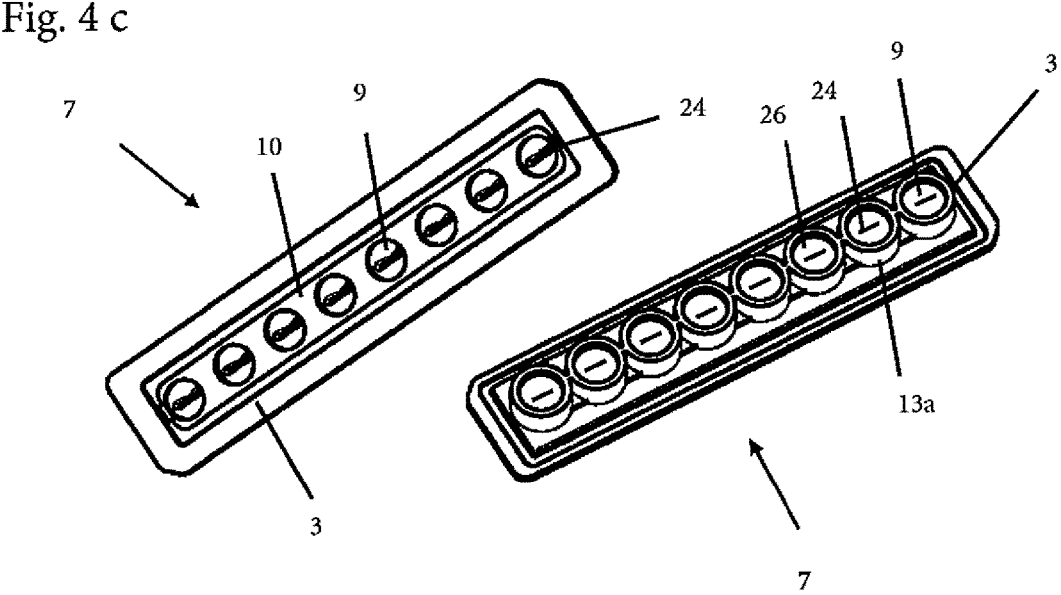

The cover 3 of the closure 7a without the strip is shown in more detail in FIG. 4a. The upper drawing is a view from below and shows the through bore holes 13, which are located on the lower surface 7a1 of the cover. The lower drawing shows the cover 3 of closure 7a as seen from the top. Pocket 14 and through bore holes 13 are visible on the upper side of cover 7a2.

Strip 12 is shown in FIG. 4h. On top is a perspective view showing the upper surface 10a of base 10 of the strip 12. Base 10 and septa 9 are shown, with the barrel 16 of the septa 9 visible. The lower drawing shows the strip 12 from below, with the lower surface 10b of base 10 to which septa 9 are attached. Septa 9 have a barrel 16, a slit 24 and a bottom 26.

The assembled closure 7 is then shown in FIG. 4c. On top is a drawing showing the upper side (or upper surface) 7c of closure 7. The cover 3 is shown with the base 10 of strip 12 seated in the pocket 14 of the cover 3. The upper side of the slits 24 of septa 9 is also seen. The lower drawing shows a view of the assembled closure 7 from the bottom. The lower side (or lower surface) 7d is shown. The cylindrical wall 13a of the through bore holes 13 can be seen. The septa 9 are seated in the through bore holes 13. The bottom 26 and the slits 24 are also shown.

Figure 5:
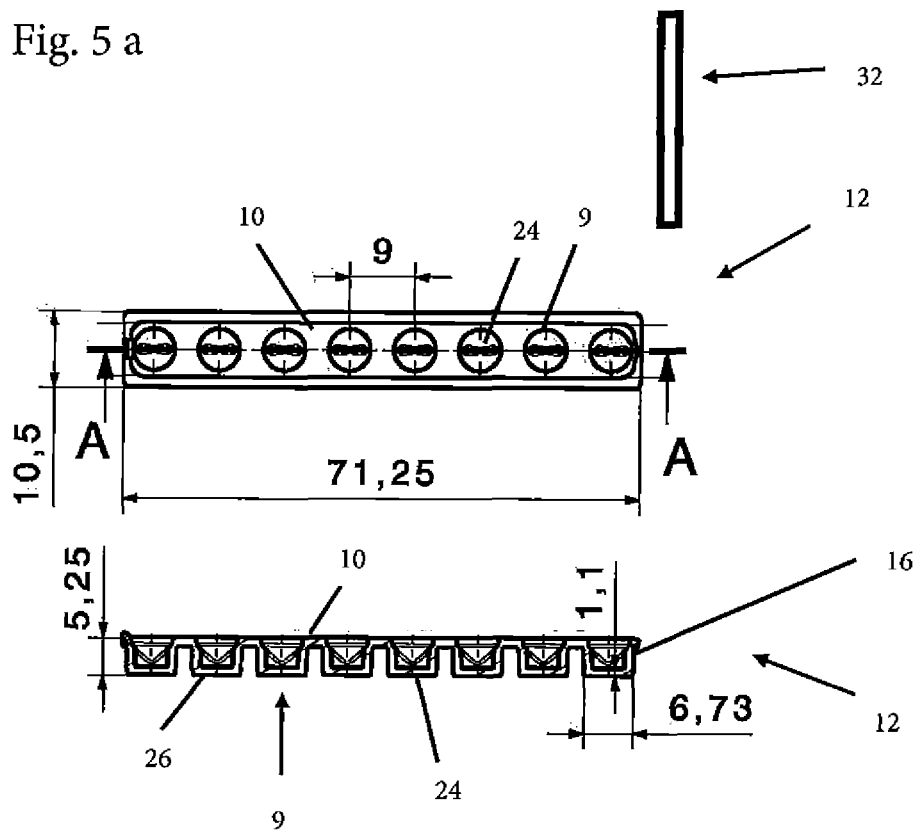
FIG. 5 a) shows the dimensions of the septa strip, b) shows the dimensions of the cover.
Figure 5:
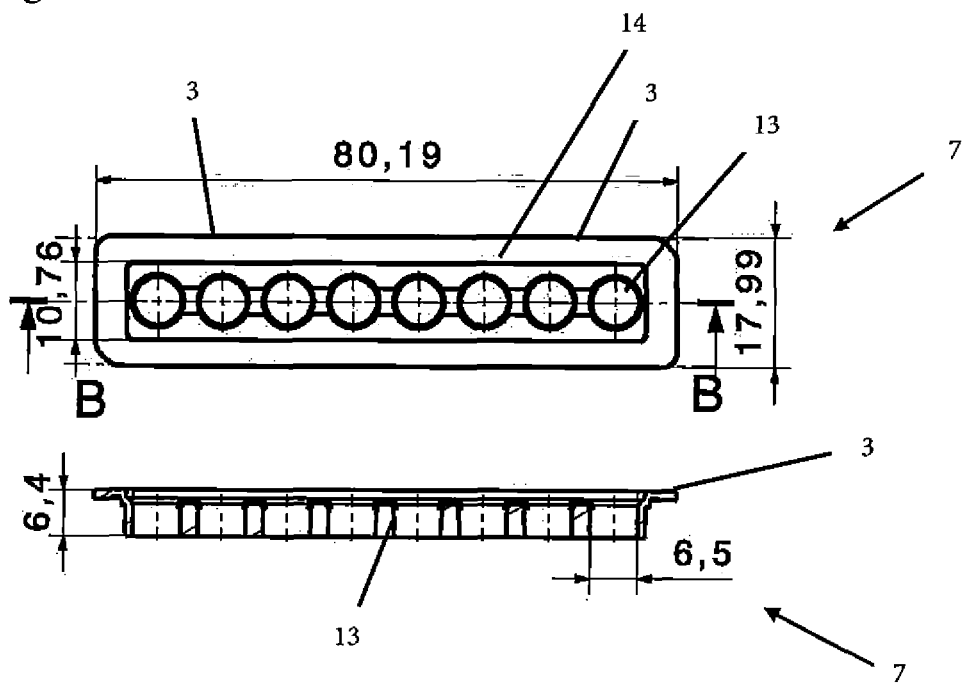

A top and side view of the strip 12 including exemplary dimensions is shown in FIG. 5a. The base 10 is shown with septa 9, slits 24 and bottom 26 are shown. Also shown is the barrel 17 of the septa 9. The distance between the outer walls of the barrel 16 is 6.73 mm. A blunt ended pipetting device 32 is also shown.

FIG. 5b shows top and side view and dimensions of the cover 3. Through bore holes 13 are shown, and also the cylindrical walls 13a of through bore holes 13. The distance between the inner walls of the cylindrical wall 13a of a through bore hole is 6.5 mm. Thus, the cylindrical wall 13a of a through bore hole 13 is 0.23 mm smaller than the outer wall of barrel 16 of the septa. This leads to a pressure being exerted by the cylindrical wall 13a on the septa 9, causing the slit 24 to close.

Figure 6:
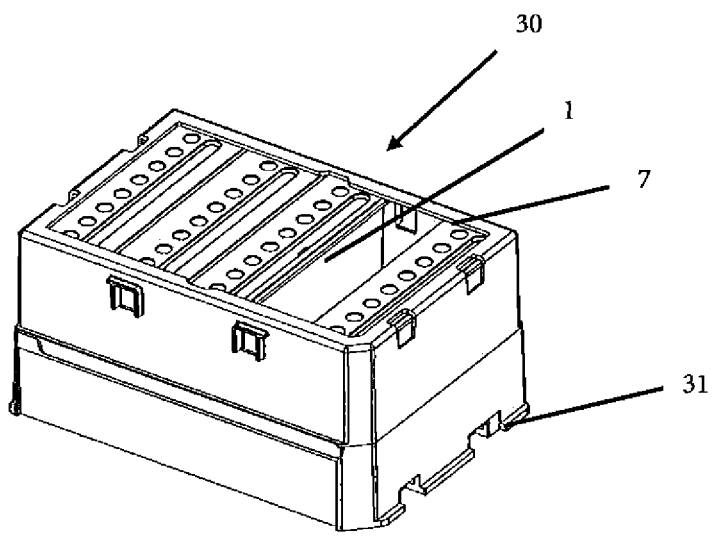
FIG. 6 shows a perspective view in a) of a cassette comprising containers with closures, and in b) a top view of the same.
Figure 6:
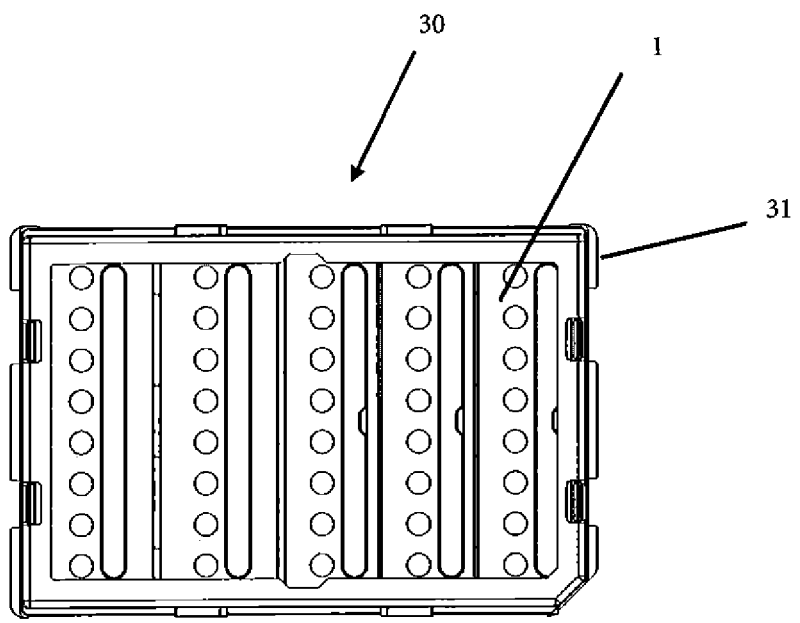

FIG. 6a shows a perspective view of a cassette 30 with a base 31 and a container 1 with closure 7 assembled in the cassette 30. FIG. 6b shows a top view of cassette 30 with containers 32.

What is claimed:

1. A closure for a container containing a reagent, said closure consisting essentially of:
   (a) a cover comprising a pocket including at least two through bore holes extending from the cover and facing the inside of said container; and
   (b) a strip bonded to said cover comprising (i) a base consisting of a stiff material, and (ii) at least two septa attached to said base, wherein said pocket is sized to match the dimensions of said base and said strip is positioned in said cover by seating the base in the pocket,
   wherein said septa are attached to one surface of said base, each septum comprises a pre-slit bottom and a barrel forming the sides of the septum, the outer diameter of the septum barrel is larger than the inner diameter of the through bore hole, and said at least two septa are configured to be press fitted into said at least two through bore holes such that a pressure exerted on the septum when the septum is press fitted into the through bore hole forms a liquid-tight seal.

2. The closure of claim 1, wherein the outer diameter of said septum is up to 50% larger than the inner diameter of the through-bore hole.

3. The closure of claim 1, wherein the septa comprise thermoplastic elastomer (TPE) or rubber and the cover and the base of the strip comprise polypropylene or a thermoplastic polymer.

4. The closure of claim 1, wherein the septa are press fitted into the through bore holes and the base of the strip is bonded to the cover of the closure.

5. The closure of claim 1, wherein said closure comprises an upper and a lower surface, wherein the upper surface of the closure is covered by a sealing foil.

6. A container comprising a vessel for holding a reagent, wherein said vessel has a closed bottom end and an open top end, and a closure according to claim 1.

7. A method of pipetting a reagent in an automated analyzer, said method comprising the steps of
   a) providing to the automated analyzer a container according to claim 6, wherein the closure of said container comprises pre-slit septa,
   b) penetrating said pre-slit septa with blunt ended pipetting devices, wherein each of the pre-slit septa comprises a slit which is longer than the diameter of each of said pipetting devices such that a pressure relief occurs upon penetration,
   c) aspirating a predetermined volume of said reagent into said pipetting device,
   d) removing said blunt-ended pipetting device, whereby a pressure exerted by the through-bore hole on the press-fitted pre-slit septum causes the pre-slit septum to close, and
   e) dispensing the aspirated reagent into a vessel.

8. The method of claim 7, wherein steps b) to e) are repeated at least once.

9. A system for pipetting reagents in an automated analyzer comprising
   a) a container according to claim 6,
   b) a pipettor for aspirating and dispensing reagents, wherein said pipettor is operatively coupled to a blunt-ended pipetting device.

10. The system of claim 9, additionally comprising a transport mechanism for transporting the container to the pipettor and away from the pipettor.

11. The system of claim 10, additionally comprising a storage for storing the container, wherein the container is returned to the storage after pipetting, and is transported back to the pipettor for pipetting.

12. A cassette comprising at least two containers according to claim 6.

13. The system of claim 9, wherein said pipetting device is a disposable pipette tip.

14. The system of claim 9, wherein the pipetting device is a blunt ended needle.

* * * * *